United States Patent [19]

Jaduszliwer et al.

[11] Patent Number: 5,674,751
[45] Date of Patent: Oct. 7, 1997

[54] DIODE LASER INTERROGATED FIBER OPTIC HYDRAZINE-FUEL SENSOR SYSTEM AND METHOD

[75] Inventors: Bernardo Jaduszliwer, Santa Monica; Charles M. Klimcak, Hawthorne, both of Calif.

[73] Assignee: The Aerospace Corporation, El Segundo, Calif.

[21] Appl. No.: 644,782

[22] Filed: May 10, 1996

Related U.S. Application Data

[62] Division of Ser. No. 490,443, Jul. 5, 1995, Pat. No. 5,567,622.

[51] Int. Cl.⁶ .................................................. G01N 21/63
[52] U.S. Cl. .................... 436/116; 422/58; 422/82.05; 422/82.06; 422/82.09; 422/82.11; 422/83; 422/88; 436/106; 436/107; 436/117; 436/167; 436/902; 250/227.14; 250/227.21; 250/231.1
[58] Field of Search .................... 422/82.05, 82.06, 422/82.09, 82.11, 83, 88, 58; 436/106, 107, 116, 117, 167, 902; 250/227.14, 227.21, 231.1

[56] References Cited

U.S. PATENT DOCUMENTS

| | | | |
|---|---|---|---|
| 3,455,656 | 7/1969 | Roberts et al. | 23/254 |
| 4,780,282 | 10/1988 | Holtzclaw et al. | 422/56 |
| 4,929,049 | 5/1990 | Le Goullon et al. | 350/96.29 |
| 5,059,790 | 10/1991 | Klainer et al. | 250/227.21 |
| 5,094,958 | 3/1992 | Klainer et al. | 436/172 |
| 5,164,588 | 11/1992 | Marcus | 250/227.21 |
| 5,212,099 | 5/1993 | Marcus | 436/172 |
| 5,244,810 | 9/1993 | Gottlieb | 436/68 |
| 5,270,537 | 12/1993 | Jacobs | 250/227.15 |
| 5,306,642 | 4/1994 | Reagen et al. | 436/106 |
| 5,307,146 | 4/1994 | Porber et al. | 356/320 |
| 5,445,795 | 8/1995 | Lancaster et al. | 422/82.11 |
| 5,460,971 | 10/1995 | Gottlieb | 436/167 |
| 5,496,997 | 3/1996 | Pope | 422/82.06 |
| 5,525,466 | 6/1996 | Slovacek et al. | 422/82.05 |
| 5,567,622 | 10/1996 | Jaduszliwer et al. | 436/106 |

*Primary Examiner*—Jill Warden
*Assistant Examiner*—Sharidan Carrillo
*Attorney, Agent, or Firm*—Derrick M. Reid

[57] ABSTRACT

A fiber optic chemical dosimeter system detects the presence of hydrazine fuels and nitrogen tetroxide and nitrogen dioxide gases that are used at rocket launch sites using colorimetric sensors that react selectively with the gases and then absorb laser light communicating through a fiber optic network having a conventional diode laser source transmitting interrogation pulses to a plurality of distributed sensors covering a wide area launch site, the sensor being reactive cladding or distal end types both providing optical reflective returns well suited for reflective near infra-red and visible-red laser interrogation by an optical time domain reflectometry monitor which compares the interrogated laser pulses with sensor returns to determine the extent and location of gas cloud exposures over the distributed wide area.

14 Claims, 4 Drawing Sheets

DIODE LASER INTERROGATED FIBER OPTIC HYDRAZINE-FUEL SENSOR SYSTEM AND METHOD

SPECIFICATION

This application is a divisional of U.S. patent application Ser. No. 08/490,443, filed Jul. 05, 1995, now U.S. Pat. No. 5,567,622.

STATEMENT OF GOVERNMENT

This invention was made with Government support under contract number F04701-88-C-0089 awarded by the Department of the Air Force. The Government has certain rights in the invention.

FIELD OF THE INVENTION

The present invention relates to hazardous gas detection sensors, systems and methods. More specifically, the present invention relates to wide area fiber optic hydrazine fuel sensors and networks.

BACKGROUND OF THE INVENTION

Hydrazine and related compounds are used as fuels for space launch vehicles. Hypergolic rocket propellants (hydrazines and nitrogen tetroxide) used in both Air Force and civilian rocket launch operations are extremely hazardous materials whose atmospheric release could present a serious threat to health and the environment. Hydrazine and its methyl-substituted derivatives [methylhydrazine (monomethylhydrazine) and 1,1-dimethylhydrazine (unsymmetrical dimethylhydrazine)], referred to herein as hydrazine-fuels, are flammable toxic substances and suspected carcinogens with current threshold limit values of one hundred parts per billion (ppb). The American Conference of Government Industrial Hygienists (ACGIH) has recommended that these exposure limits be lowered to ten ppb for all hydrazines. Similarly, nitrogen tetroxide is a hazardous material, being a strong oxidizer with a threshold limit value of three ppm. It is imperative that accidental vapor and liquid releases of these materials be rapidly identified and located to minimize exposure of military and civilian personnel and native wildlife to propellant vapor, and to facilitate remedial cleanup operations. Hence, hydrazine fuel vapors are highly toxic, with maximum exposure levels, averaged over eight hours, likely to be set as low as ten parts per billion. Regulatory compliance requires the detection of hydrazine fuel vapors with enough sensitivity to trigger alarms before those exposure levels are reached. Possible sources of hydrazine fuel vapor releases are widely dispersed through launch facilities, which typically span large land areas.

Monitoring of hydrazine fuel vapors is currently accomplished by fixed or portable instruments based on electrochemical sensors or colorimetric chemical indicators. Electrochemical hydrazine-fuel monitors measure electric current produced when a hydrazine-fuel is oxidized in an electrochemical cell, but such monitors are not suitable for monitoring gaseous hydrazine-fuels over wide areas.

Colorimetric monitors use moving paper tapes impregnated with reagents which change color in the presence of hydrazine fuel vapors. Changes in color are automatically detected by photometry. Hydrazine-fuel area monitors using colorimetry have been made by GMD Systems Inc. The colorimetric hydrazine-fuel monitors use paper tape impregnated with phosphomolybdic acid (PMA) which moves at a constant rate past an air intake. When exposed to a hydrazine-fuel vapor, the tape changes color. The change in color is detected by comparing light reflected by the tape prior to and after exposure to the air intake. These devices are large, expensive, contain moving parts, require frequent maintenance and are not well suited for systems-oriented operations. Monitors using these sensors are cumbersome, require high maintenance, are not well suited for centralized network operation over a large area and are unable to detect hydrazine fuel vapors below twenty parts per billion.

Another type of colorimetric monitor are the paper cardboard badges which have been used as personal hydrazine-fuel monitors for launch personnel wearing the badges about launch sites. The colorimetric dosimeter badges are used for additional protection. These personnel badges use paper impregnated with reagents. Changes in color indicating exposure to hydrazine fuels are detected visually. The cardboard badges contain pieces of paper impregnated with colorimetric hydrazine-fuel indicators. Usually, more than one indicator is used to provide assurance against false positives. Vanillin, dinitrobenzaldehyde and para-dimethylaminobenzaldehyde are generally used as indicators. The hydrazine-fuel exposure dose is estimated by visually comparing the indicator-impregnated pieces of paper with a color chart. Badges provide only an after-exposure indication of hydrazine-fuel exposure, and in most cases will not help in locating the source of hydrazine fuel vapor leaks.

Fiber optic-based personal dosimeters have been developed. Geo-Centers, Inc. developed a personal hydrazine dosimeter based on an optical fiber chemical optrode. The dosimeter consists on a short length of porous optical fiber impregnated with the colorimetric reagent vanillin. When exposed to hydrazine, vanillin turns yellow by strongly absorbing blue light. The dosimeter operates by absorption with a blue light source, for example, blue light-emitting diode (LED) at one end and a photodetector at the other. Exposure of the fiber to hydrazine causes the transmission of light within the fiber to decrease sharply, and thus reduces the photodetector output signal. This device uses the length of a modified optical fiber incorporating a colorimetric hydrazine indicator as the hydrazine sensor. A disadvantage of this device is that it can not be used to accurately locate a poisonous hydrazine cloud. This device operates by monitoring the light transmitted through the fiber, rather than the backreflected light at a well defined point. Thus, this device is basically a single-sensor device, not compatible with multiple-point detection by laser interrogation. In particular, it can not be interrogated using the Optical Time Domain Reflectometry (OTDR) techniques for multiple-point detection for determining the exact location and extent of a hydrazine-fuel release. The choice of vanillin as a hydrazine indicator dictates that the sensor must be interrogated with blue light, instead of visible red or near-infrared light. The limited use of only blue light has two additional disadvantages which prevent the use of the Geo-Centers sensor in a multiple-point hydrazine-fuel-monitoring network. Firstly, sources of blue light are blue LEDs which typically do not produce sufficient light intensity to interrogate multiple sensors. Secondly, blue light is not transmitted very well by optical fiber which limits severely how far a sensing element can be from the light source and the photodetector. The use of vanillin hydrazine sensors is unsuitable in a multiple point hydrazine-fuel-monitoring network where high intensity illuminating laser light is required to propagate over the wide area.

United States Statutory Invention Registration # H1297, "Detection Device for Hazardous Materials", J. K. Partin and A. Grey, Issued Apr. 5, 1990, describes a fiber optic dosimeter suitable for the detection of hydrazine vapors. It uses evanescent wave absorption in an optical fiber, and uses colorimetric indicator techniques. The reagent used to detect the presence of hydrazine is nitrobenzaldehyde, which is not suitable for interrogation by diode lasers, because after hydrazine exposure, it absorbs light in the blue region of the spectrum, rather than in the visible red or near infra-red. A tungsten/halogen lamp is used but it cannot be pigtailed to an optical fiber and requires the use of an alignment micrometer stage and a focusing lens. The dosimeter detects the presence of hydrazine by absorption, and not by reflection. Thus, this dosimeter cannot be used with optical time domain reflectometry techniques to interrogate the sensor, and the device is only capable of sensing hydrazine at a single point. This dosimeter is not suitable for use in a multipoint fiber optic sensor network. Also, in order to obtain a reference signal measuring how bright the lamp is, the dosimeter detects the red component of the lamp light which propagates through the fiber essentially unattenuated, whether hydrazine is present or not. In order to do so, the dosimeter needs a somewhat complicated detector involving a beam splitter, two interference filters (one for blue light and one for red light), two photodiodes and a second alignment micrometer stage.

U.S. Pat. No. 5,059,790 "Reservoir Fiber Optic Chemical Sensors", Klainer et al., Issued Oct. 22 1991, and U.S. Pat. No. 5,116,759, "Reservoir Chemical Sensors", Klainer et al., Issued May 26 1992, describe a general class of chemical sensors interrogated by optical fibers in which the indicator chemistry takes place in the liquid phase within a special reservoir. The chemical species being sensed enters through a specialized permeable membrane. The selected membrane is for sensing a number of chemical species, amongst which is hydrazine. These systems use a colorimetric indicator general technique. The reagent employed for sensing hydrazine is a cupric neocuproine solution which, upon exposure to hydrazine, absorbs light in the blue region of the spectrum. Optical fibers are only used to convey light in and out of the sensing reservoir. These systems are not suitable for wide area hydrazine detection using a network of distributed sensors adapted for use with conventional visible red and near infra-red lasers.

Evanescent wave fiber optic sensors are well known. Sol-gel glass techniques have been used to make evanescent wave fiber optic chemical sensors. Sol-gel pourous glass sensors have been used in medical applications to detect various gases in and the pH of circulating blood. A catheterized optical fiber with a single distal end sensor has been used. These sensors typically use short wavelength blue light lamps for real time interrogation. These sensors have not been adapted to wide area detection of hydrazine-fuels using interrogating lasers.

Most available hydrazine-fuel indicators display changes in the blue wavelength range, for which no convenient laser sources exist, and which is strongly absorbed in optical fibers. There are no convenient optical indicators outside the blue wavelength range, rendering hydrazine-fuel optical detection unsuitable for low cost conventional visible red and near infra-red lasers. These hydrazine-fuel detectors are not adaptable to fiber optic networks for detecting hydrazine-fuels over a wide area. These and other disadvantages are solved or reduced using the present invention.

SUMMARY OF THE INVENTION

An object of the present invention is to provide a sensor for hydrazine, monomethylhydrazine, or unsymmetrical dimethylhydrazine that is suitable for use with optical fibers.

Another object of the present invention is to provide a colorimetric sensor suitable for interrogation by a diode laser through fiber optics.

Another object of the present invention is to provide a sensor for hydrazine, monomethylhydrazine, or unsymmetrical dimethylhydrazine which is responsive to visible red and near infra-red light illumination.

Yet another object of the present invention is the use of a plurality of hydrazine-fuel sensors disposed at a respective plurality of distal ends of a fiber optic network for detecting the presence of hydrazine, monomethylhydrazine, or unsymmetrical dimethylhydrazine over a wide area.

Still another object of the present invention is the use of a plurality of hydrazine-fuel sensors disposed at a respective plurality of distal ends of fiber optic networks and illuminated by and reflecting laser pulses for detecting the presence of hydrazine, monomethylhydrazine, or unsymmetrical dimethylhydrazine over a wide area using optical time domain reflectometry techniques.

Still a further object of the present invention is to provide a method of detecting the presence of a gas over a wide area using a diode laser that provides pulses to a fiber optic network having a plurality of distributed PMA sensors.

Yet another object of the present invention is to provide a method for calibrating a diode laser, colorimetric, fiber optic distributive sensor system for detecting the presence of gases over a wide area.

Yet a further object of the present invention is to provide a method to verify the accuracy of a colorimetric sensor and monitoring system using reagent bath techniques.

Another object of the present invention is to provide a system and method of detecting the presence of nitrogen tetroxide or nitrogen dioxide by using a PMA sensor previously exposed to a hydrazine-fuel.

Yet another object of the present invention is to provide a sensor for detecting nitrogen tetroxide or nitrogen dioxide.

Still another object of the present invention is to provide a sensor with a phosphomolybdic acid sensor for use as a sensor for hydrazine, monomethylhydrazine, or unsymmetrical dimethylhydrazine or as a nitrogen tetroxide or nitrogen dioxide sensor.

The present inventions cover a sensor device and fiber optic network that is basically a multiple sensor network for multiple-point detection to assure launch personnel safety, as well as early detection and remediation of hydrazine fuel vapor leaks, in a systems approach, using a network of multiple sensors having adequate sensitivity and dynamic range, deployed through the whole "at risk" area and transmitting data on hydrazine fuel vapor concentration in real time to a central monitoring facility. The present inventions cover fiber optic sensors and networks that fulfill these requirements. The term "hydrazinefuel(s)" as used herein means hydrazine, monomethylhydrazine, and unsymmetrical dimethylhydrazine, in any combination, or separately.

The fiber optic chemical dosimeter network system detects leaks of toxic vapors or hazardous substances at remote sensor locations during launch operations. The network preferably detects vapors of the hypergolic rocket propellants, but may also be flexible enough to permit incorporation of sensors for other liquids and vapors. The fiber optic system will permit centralized monitoring of numerous sites on a launch complex (e.g., fuel and oxidizer storage areas, payload assembly areas, launch vehicle propellant tanks and associated transport lines, personnel areas, base perimeter, aquifers, estuaries, etc). This system will enhance the ability to verify compliance with existing and anticipated environmental regulations and provide rapid identification of the source and strength of accidental propellant releases. Additionally, the system can be used to detect residual propellant vapor emanating from scrubbing towers during normal venting operations.

The fiber optic dosimeter network system detects hydrazine-fuel vapors. The method employs colorimetric hydrazine-fuel recognition chemistry incorporated within discrete fiber optic dosimeter sensors located at the distal ends of branches of a fiber optic network. The chemical reaction within the sensors produces a change in absorption and thus the intensity of laser light retro-reflected from the dosimeter sensors to a receiving photodetector when sufficient hydrazine-fuel vapor has reacted with the colorimetric reagent of the sensors. The sensors may use chemical reagents that react reversibly with hydrazine-fuel vapors to develop hydrazine-fuel vapor concentration sensors that could be deployed in a similar fashion on a remote fiber optic network to detect hydrazine-fuel vapors in the ppb regime.

The present inventions use fibers optics to transmit detection pulses to a plurality of sensors for multiple point detection. The inventive system can interrogate the multiple hydrazine-fuel sensors using the Optical Time Domain Reflectometry technique for multiple-point detection for determining the exact location and extent of a hydrazine-fuel release. The red or near infrared light are used to interrogate the sensors. The network of sensors can be interrogated by red or infrared light, by conventional diode lasers which produce sufficient high light intensities. This light has sufficient intensity to propagate through kilometers of fiber, allowing adaptation of the invention to wide area networks in extended, multiple-point, hydrazine-fuel-monitoring networks.

The sensor of the present inventions includes an identifying colorimetric indicator which, upon reaction with a hydrazine-fuel, would display significant changes in its absorption spectrum in the infra-red and near infrared wavelength range for which reliable, small, low cost diode laser sources are available and for which optimal light propagation through optical fibers obtains. The sensor allows the detection of hydrazine fuel vapors at multiple points over a wide area. Sensors are designed to be interconnected by a fiber optic network, and interrogated by low cost, commercially available diode lasers which operate within the best wavelength range for transmission through optical fibers.

The inventions enable the remote detection of hydrazine fuel vapors at multiple locations with a dose sensitivity of a few parts per billion hours. The sensors have cost effective construction and are less obtrusive than either electrochemical or colorimetric fixed-point monitoring stations. Multiple sensors can be distributed over a wide area and monitored automatically from a single control station. Sensor multiplicity allows mapping of the hydrazine fuel vapor plume and faster source identification. This approach, allowing real-time surveillance for the presence of hydrazine fuel vapors over a wide area, is inherently safer than after-the-fact reading of personnel exposure badges.

The inventive system works by measuring changes in the intensity of light reflected back by fiber optic colorimetric sensors upon sensor exposure to a hydrazine fuel. Phosphomolybdic acid (PMA) is used as the hydrazine-fuel indicator, immobilized either in a porous glass matrix which may be prepared by the sol-gel technique, or a polymer matrix like polyvinyl acetate. The sensors may have different configurations including an evanescent wave fiber optic colorimetric reactive cladding hydrazine-fuel sensor or an evanescent wave fiber optic reactive distal end hydrazine-fuel sensor. In an unexposed state, the PMA-impregnated matrix is yellow. After exposure to hydrazine fuel vapors, the matrix turns dark blue, and becomes a strong absorber of red and infrared light. One or more sensors are optically coupled to a fiber optic line, and interrogated by red or infrared light pulses produced by inexpensive diode lasers. The back-reflected pulses may be detected using the Optical Time Domain Reflectometry (OTDR) technique. In its unexposed (yellow) state, a sensor reflects back most of the incoming light. In its exposed (blue) state, less light is reflected. The reduction in the fraction of light reflected back measures the hydrazine-fuel dose absorbed by the sensor, and calibration experiments allow the derivation of the dose from the fractional reduction of sensor reflectivity. Such calibration provides dose sensitivity of three parts per billion-hours for the reactive cladding hydrazine-fuel sensor and seven parts per billion hour for the reactive distal end sensor. The sensitivity can be lowered by reducing the PMA concentration, and a combination of sensors having different sensitivities can provide measurement capabilities over very large dynamic ranges.

A sensor in a blue state after being exposed to a hydrazine-fuel will return to a yellow state when exposed to nitrogen tetroxide or nitrogen dioxide. Thus, blue-state sensors saturated with a hydrazine-fuel as a reducing agent can also be interrogated by red or infrared light pulses produced by the inexpensive diode lasers to detect the presence of nitrogen tetroxide or nitrogen dioxide. Upon exposure to nitrogen tetroxide or nitrogen dioxide, the fraction of light reflected back will increase. This increase in the fraction of light reflected, measures the nitrogen tetroxide or nitrogen dioxide dose absorbed by the sensors and calibration allows for the derivation of the dose from the fractional increase of sensor optical reflectivity.

The fiber optic sensor's specific design enables integration in a fiber optic sensing network to detect hydrazine-fuel vapors at multiple points, and is particularly well suited for interrogation using the OTDR technique. The PMA reagent is used in a yellow state as a hydrazine-fuel colorimetric indicator in conjunction with interrogation of the sensors by diode lasers emitting near infrared or red light pulses. The PMA reagent is also used in a blue state saturated with a hydrazine fuel as a nitrogen tetroxide and nitrogen dioxide colorimetric indicator in conjunction with interrogation of the sensor by diode lasers emitting near infrared or visible red light pulses. Pigtailed lasers can be coupled to fiber very easily, and red or infrared light absorption within the fiber is very low. Other, commonly used colorimetric indicators for hydrazine fuels must be interrogated with shorter wavelength light, requiring the use of lasers which are much more expensive, much larger, more difficult to couple to optical fiber and less reliable than diode lasers. Additionally, at those shorter wavelengths light does not propagate through optical fibers as efficiently. During exposure to hydrazine fuels, PMA spectral reflectivity changes are well suited for use in a fiber optic network communicating infra-red and near infrared wavelengths. We use a porous glass or polymer matrix impregnated with PMA as a reactive cladding or distal termination in our hydrazine sensor. These combinations of matrix, colorimetric reagent and configuration results in sensors having very high dose sensitivity. These and other advantages will become more apparent in the following detailed description of the preferred embodiment.

DETAILED DESCRIPTION OF THE PREFERRED EMBODIMENT

Figure 1:
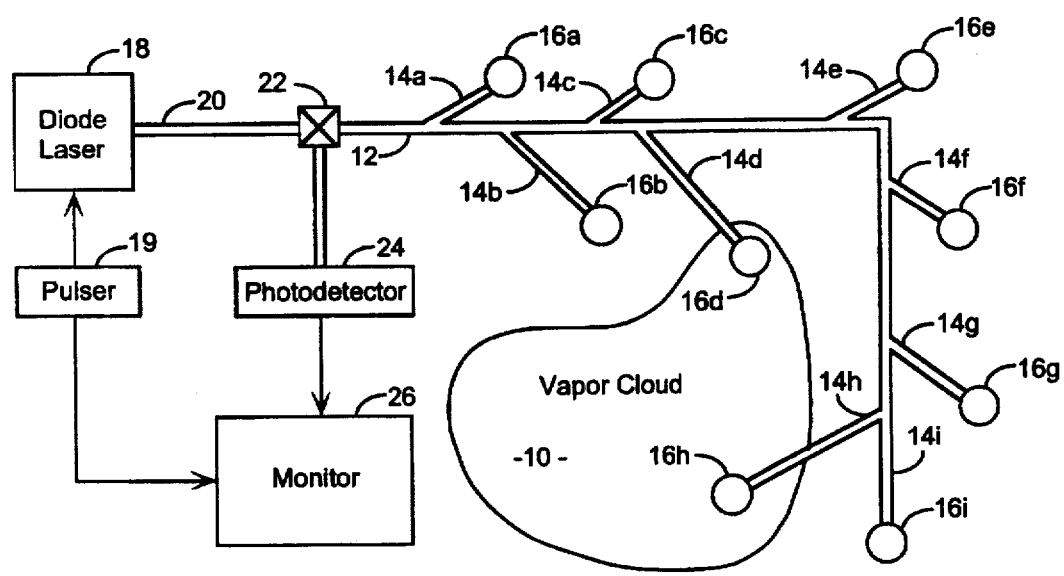
FIG. 1 is a block diagram of an intensity based fiber optic dosimeter network.
Figure 2:
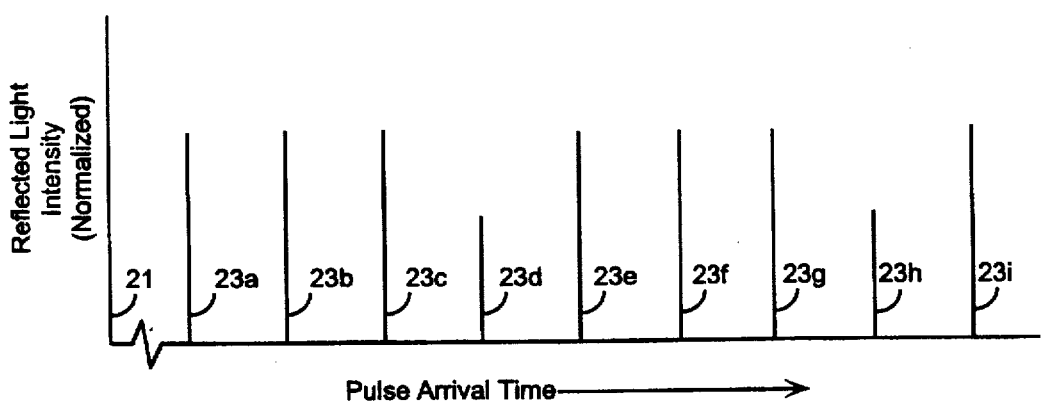
FIG. 2 is graph of an optical time domain reflectometer display of reflected laser pulses in an intensity based fiber optic dosimeter network.

Referring to FIGS 1 and 2, an intensity-based fiber optic chemical dosimeter network system is shown in FIG. 1 and is used for the remote detection of hydrazine-fuel propellant vapor clouds 10 which may leak from rocket-launched space vehicles and emergency power units used in airplanes. The fiber optic chemical dosimeter network system is used for the remote detection of toxic rocket propellant vapors, such as hydrazine and its derivatives, nitrogen tetroxide, and nitrogen dioxide which are used at Air Force and civilian rocket launch sites. The system uses one or more fiber optic networks 12 which typically includes a fiber split into a plurality of fiber optic branches 14a–i each having at each of its respective distal ends a respective fiber optic colorimetric sensor 16a–i that selectively reacts irreversibly with the propellant vapors 10 to yield chemical compounds within the sensors 16 that absorb laser light communicated from a laser 18 through the fiber optic 12 and branches 14 to sensors 16. The sensors 16 reflect laser light pulses having intensities dependent upon the presence of the hydrazine fuel. The system includes a pulser 19 for activating the laser 18 and providing an optical reference, an optical trunk 20 for receiving a laser pulse 21 from the laser 18, an optical coupler 22 for communicating the laser pulse 21 into the fiber optic network 12 and for communicating reflected pulses 23a–i respectively from sensors 16a–i to a photodetector 24 communicating corresponding electrical pulses to a monitor 26 which compares the reflected pulses 23 to the laser pulse 21 by reference to the pulser 19. By time domain reflectometry analysis, the presence of the hydrazine fuel can be determined. As shown, detectors 16d and 16h of FIG. 1 are exposed to the hydrazine fuel vapor cloud 10 and the corresponding reflected pulses 23d and 23h of FIG. 2 have attenuated amplitudes.

Remote detection of the hydrazine vapor 10 in the few hundreds of parts per billion minutes, (ppb-min) integrated dose regimes may be realized by a network having a fiber 12 that may be, for example, one kilometer in length and used with a low power ten milliwatt diode laser 18. The fiber optic dosimeter network may be expanded to have many fibers 12 in a multiplexed system containing hundreds of branches 14 and sensors 16 for vapor detection over a plurality of wide areas. The performance of a field-scale remote fiber optic detection network is enhanced by discrete chemical vapor sensors 16, optic fibers 12 and branches 14 connected in a variety of ways including serial, parallel, or hybrid serial/parallel topologies to provide flexibility for detection over many different predetermined wide areas which may have complex three-dimensional topography.

The sensors 16 are interconnected by a fiber optic network 12. The laser 18 is the preferred light source because it can provide an intense light source emitted in one direction into the optic fiber network 12 for high illumination efficiency. The laser 18 interrogates the sensors 16 at distal ends of the several branches 14 of the fiber network 12. The network 12 can be very long in length. The diode laser 18 provides a high population of electron-hole pairs providing cascaded photo emissions which become a laser pulse 21 of monochromatic light centered about a predetermined wavelength characteristic of the electron-hole pairs. The diode laser 18 preferably provides near infrared light between 700–1000 nm or visible light between 650–700 nm, particularly visible red light at 670 nm. Visible red and near infrared light wavelengths are efficiently transmitted during propagation without serious degradation along the length of the optic fiber network 12 by absorption by the optic fibers 12. Preferred wavelengths between 650 and 1000 nm correspond well to available inexpensive commercial laser diodes, as well as efficient light transmission through the fiber optics.

The operation of the system starts with a short pulse of laser light 21, preferably at about ten nanoseconds from, preferably, either a visible, 680 nanometer or near infrared, 780 nanometer, diode laser 18 communicated into the fiber optic trunk line 20 that transmits the laser pulse 21 to hydrazine-fuel dosimeter sensors 16 located at numerous distal points within a launch complex. The laser light pulse 21 is retro-reflected from these dosimeter sensors 16 as reflected pulses 23 which are detected by the photodetector 24 which may be a photomultiplier tube and displayed by the monitor 26 which may be an optical time domain reflectometer operating in a return loss mode to yield a plot of the returned light intensity versus its arrival time at the photodetector as shown in FIG. 2.

The integrated doses, that is, the concentrations over time of hydrazine fuel received by the dosimeter sensors are determined from the intensity of the returned light pulses while identification of the dosimeters is determined by the pulse arrival time order. For example, the fourth and eight return light pulses 23d and 23h in the trace of FIG. 2 exhibits a reduced intensity relative to the other pulses due to the close proximity of the fourth and eight dosimeter sensor to the depicted hydrazine-fuel vapor cloud 10.

To assess the feasibility of deploying a field-scale one kilometer dosimeter network, a parametric computer model of a multimode fiber optic sensor network may be used. This model incorporates all pertinent aspects of detection including laser power, wavelength, propagation losses, coupler insertion losses, dosimeter responsivity, photodetector responsivity, intrinsic photodetector noise, photon statistical noise, laser intensity referencing, electronic bandwidth, multimodal and material dispersion, desired spatial resolution, and sensor/dosimeter deployment topology (i. e., serial, parallel, hybrid serial/parallel). One such model indicates that a five percent change in the return signal level from an individual dosimeter could be observed with a fiber optic network composed of one hundred sensors 16 in a parallel star configuration, having a trunk length of one kilometer using a ten milliwatt 680 nanometer diode laser 18. Although laboratory measurements are easily capable of detecting much smaller intensity changes, a field device that triggers warnings at fractional intensity changes less than five percent may increase false alarm rates. The computed signal to noise ratio on the returned light signal with direct detection is one hundred with this exemplar system, yielding a signal to noise ratio of five on the observed five percent change level.

Referring to FIGS. 1, 2, 3 and 4, preferably the sensors 16 are fabricated by dispersing a reagent within either a porous cladding or a porous distal end coating, that is, prepared by a low temperature sol-gel technique. Several recognition chemistries for hydrazine-fuel detection may be used. Chemical detection is based on the selective reaction of a hydrazine fuel with a colorimetric reagent to produce a compound that absorbs the laser light pulse 21. The preferred reagent for reaction with the hydrazine fuels is phosphomolybdic acid (PMA) used in the fabrication of the dosimeter sensors 16. PMA can be used to detect all three hydrazine fuels. Phosphomolybdic acid is a bright yellow oxidizing agent that reacts with the hydrazine fuels to form several blue molybdenum oxides and hydroxides that strongly absorb visible red and near infrared light. PMA is a large complex heteropolyatomic species containing twelve moly-trioxide molecules surrounding a central phosphate anion with numerous waters of hydration intercalated within the structure. The explicit chemical form of the blue reduced oxides is not known. In a normal condition, PMA has a bright yellow color and a good reflector of red light. After exposure to a hydrazine fuel, the PMA becomes a strong absorber of red light and appears deep blue.

The spectral wavelength changes of reflected light of phosphomolybdic acid after hydrazine-fuel exposure are between 500 nm to 2000 nm. A normalized wavelength change in reflectivity of PMA-coated filter paper that has been exposed to one ppm hydrazine vapor for one hour shows good visible red and infra-red variation. The reflectivity spectrum is derived from separate measurements of the reflection spectra of unexposed and exposed PMA-coated filter paper with a dual beam, integrating sphere reflectometer. The change in reflectivity is caused by exposure to hydrazine fuel vapor divided by the unexposed reflectivity. A very broad action spectrum occurs over an ideal wavelength range accessible with visible and near infrared diode lasers. While the reaction between a hydrazine fuel and PMA is irreversible and thus suitable only for use as a dosimeter sensor, the reaction can be chemically reversed by oxidizing the reacted dosimeter with nitrogen-dioxide gas to regenerate the yellow PMA species. A PMA-dosimeter that has been reduced to the blue state by an intentional exposure to hydrazine fuel vapor could be used to detect leaks of nitrogen dioxide, a spontaneous dissociation product of the hypergolic propellant oxidizer nitrogen tetroxide. Exposure of a reduced "blue PMA" coating to nitrogen dioxide or nitrogen tetroxide vapor transforms it into a bright yellow coating that can be reduced again to the blue state by a re-exposure to a hydrazine fuel. A hydrazine-fuel dosimeter sensor can be a resettable device using nitrogen dioxide or a nitrogen dioxide dosimeter sensor resettable by reacting with a hydrazine fuel. The sensor 16 contains the immobilized reagent used to detect the presence of a hydrazine fuel in a yellow state or nitrogen dioxide or nitrogen tetroxide in a blue state. Standard acid-catalyzed sol-gel coating techniques may be used for reagent immobilization using procedures similar to those used in the fiber optic chemical sensor construction and manufacture. As examples, both reactive cladding dosimeter sensors and distal end dosimeter sensors 16 may be constructed.

Figure 3:
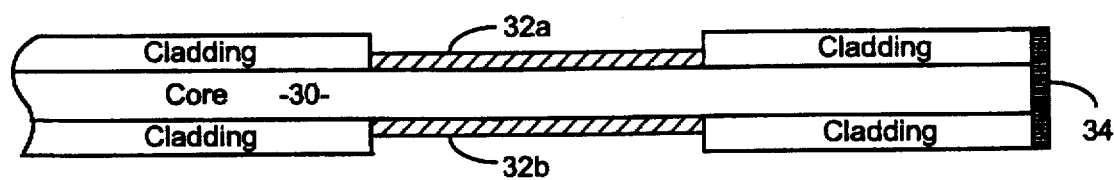
FIG. 3 depicts an evanescent wave fiber optic reactive cladding hydrazine-fuel sensor coupled to an optical fiber network and having a fiber core, fiber cladding, PMA-impregnated matrix reactive cladding with a high reflectivity termination.

Referring to FIG. 3, a reactive cladding may be produced from a sol having a $H_2O$:Si molar ratio of six. A mixture of fifty-two ml tetra-ethylortho-silicate, one-hundred ml ethanol, and twenty-five ml 0.1N HCl is sonicated in a Parafilm sealed vessel for seventeen hours at 50° C. in a ultrasonic bath. Phosphomolybdic acid is then added to this precursor sol at a concentration of 2.4 g/l. Reactive cladding dosimeter sensors are fabricated preferably from high OH TECS (a Trademark of 3M Company) Hard Clad step index silica fiber having a core 30 with a core diameter of two-hundred microns. Ten cm of cladding near the end of an optic branch may be removed by rubbing with an acetone-dampened lens tissue. The de-clad fiber 32a–b should be immersed in hot, 60° C., Chromerge for thirty minutes, rinsed with copious amounts of deionized water and microscopically inspected for residual cladding. The de-clad region 32 is then re-immersed in hot Chromerge for an additional thirty minutes, rinsed with water, and immersed in the PMA/Sol precursor solution. The region 32 should be allowed to remain in the solution for thirty minutes before withdrawing it at a rate of 10 cm/minute into a sealed chamber. The coated fiber should be first dried in ethanolic air in this chamber for forty hours. The coated fiber should then be dried in an oven under an air atmosphere at 70° C. for twenty hours. Detection with the reactive cladding dosimeter sensors relies on evanescent wave coupling of the laser light propagating through the dosimeter sensor region 32. Epoxy 34 was applied to the cleaved distal end of the reactive cladding dosimeter to shield the silica surface from hydrazine fuel vapor and to provide a stable retro-reflected intensity from the silica/epoxy interface. The intensity of the reflection can be considerably enhanced (by four times that of a freshly cleaved fiber) if the epoxy coating is formed with a rounded surface of the appropriate shape. Alternatively, one could deposit a reflective metal, such as a silver coating on the distal surface to produce high retro-reflected intensity.

Figure 4:
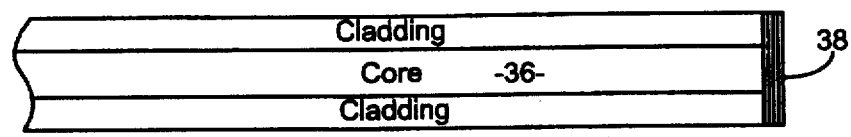
FIG. 4 depicts an evanescent wave fiber optic reactive distal end hydrazine-fuel sensor coupled to an optical fiber network and having a fiber core, fiber cladding and a PMA-impregnated matrix reactive distal termination.

Referring to FIG. 4, a distal end coated dosimeter sensor may be produced with a sol having a $H_2O$:Si ratio of two that is prepared. Fifty-two ml tetraethylorthosilicate, 6.3 ml water, thirty-nine ml ethanol, and 2.5 ml of 1.0N HCl is mixed and sonicated in a Parafilm sealed vessel for twenty hours at 50° C. in an ultrasonic bath. The sol is then evaporated in an open vessel until its viscosity, at ten 10 cp, is sufficient for producing an end coated dosimeter. Phosphomolybdic acid is added to this precursor sol at a concentration of 2.4 g/l. The distal end dosimeter sensor 38 is then attached to the end of Spectran graded index silica/silica fiber having a core 36 with a fifty micron core diameter and a communications bandwidth of 1.2 GHz-km at 850 nm. A dip-coating and drying procedure is used to produce the distal end 38 dosimeter sensor which is similar to that used for the active region 32 of reactive cladding dosimeter sensor. Reflections at the silica/sol-gel and sol-gel/air interfaces provided the retro-reflected return light pulse from the dosimeter sensor. The retro-reflected intensity should be continuously monitored during all drying and epoxying operations to observe the occurrence of any catastrophic failures due to sol-gel cracking.

Figure 5:
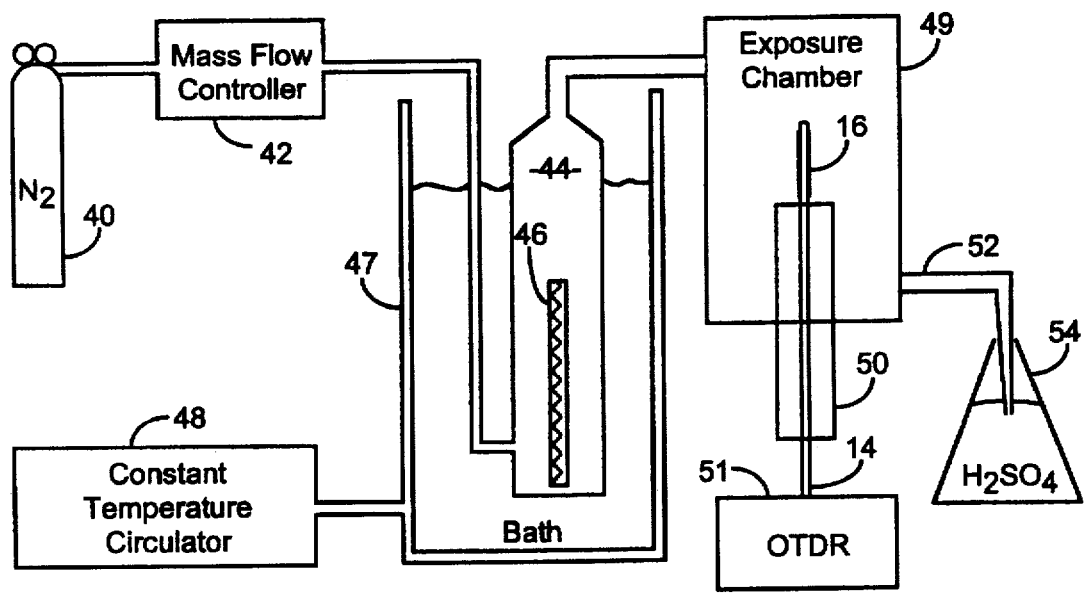
FIG. 5 is a schematic diagram of a hydrazine-fuel dosimeter verification and calibration apparatus.
Figure 6:
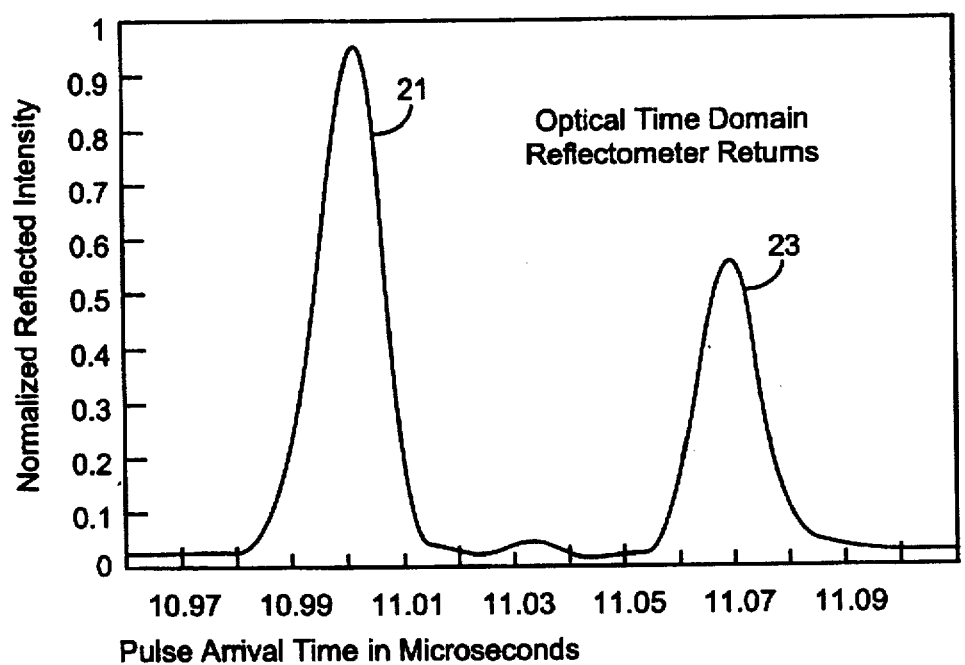
FIG. 6 is a graph depicting optical time domain reflectometer returns of sensor signals.

Referring to FIGS. 5 and 6, calibration of the dosimeter sensor response to a hydrazine fuel vapor may be performed prior to use in a distributed network. A calibration system may include a flow source 40 of $N_2$ gas at an actively regulated flow rate of 200 ml/min by a mass flow controller 42 for delivery of $N_2$ into a thermostated mixing vessel 44 containing a hydrazine-fuel permeation tube 46. Hydrazine-fuel permeation tubes are manufactured by Kintek Laboratories of La Marque Tex., for example, that emit a low flux (typically 100 ng/min) of hydrazine-fuel vapor into a mixing vessel 44. The vessel 44 is disposed in a circulating bath 47 controlled by a constant temperature circulator 48 which maintains the bath 47 at a constant temperature preferably at 25° C. Gaseous mixtures of nitrogen and the hydrazine-fuel in the mixing chamber 44 are then directed into a dosimeter exposure chamber 49 whose surfaces have been coated with paraffin in order to minimize parasitic losses of hydrazine-fuel vapor to the walls. A dosimeter hydrazine fuel sensor 16 is disposed at the end of a optic fiber 14 which is protected by a sleeve 50 which is fed through and into the exposure chamber 49. The length of the optic fiber 14 may be equal to the length as used in a network to be installed, including all other attached serial and parallel fibers 14 and sensors 16, not shown, so as to provide a exact working configuration for purposes of sensor calibration. Alternatively, a sensor may be calibrated using a predetermined length of branch optic fiber, and the calibration adjusted to account for fiber line losses that are predicted in 4 an actual configuration to be installed. The optical time domain reflectometer 51 is used to calibrate the sensor 16. The reflectometer 51 would include a laser 18, trunk line 20, pulser 19, coupler 22, photodetector 24, 12 and monitor 26 as shown in FIG. 1. The reflectometer 51 measures return time displacements 8 and amplitudes at various exposures. The mixing vessel 44 typically provides a preferred average hydrazine-fuel vapor concentration in the exposure chamber 49 of two-hundred ppb of the hydrazine fuel in nitrogen carrier gas. Hydrazine fuel vapor flowing from the chamber 49 can be collected by bubbling the effluent vapor through a small tube 52 into a vessel 54 containing 0.1N sulfuric acid. A measured amount of the collected sulfuric acid sample may be analyzed using standard spectrochemical techniques employing colorimetric reagents to determine the average concentration of the hydrazine fuel in the chamber 49 during the collection and dosimeter exposure periods. For example, Hydraver 2, manufactured by Hach Company, may be used as a colorimetric reagent for hydrazine. A known quantity of reagent is added to a measured amount of acid solution to provide a solution that changes color upon exposure to hydrazine vapor. The color developed may be compared for colorimetric match to solutions containing known quantities of hydrazine and the reagent to determine the concentration of hydrazine in the gas stream. The reflectometer records the amplitude attenuation produced in the fiber optic sensor which is then calibrated to the amount of hydrazine exposure.

Figure 7:
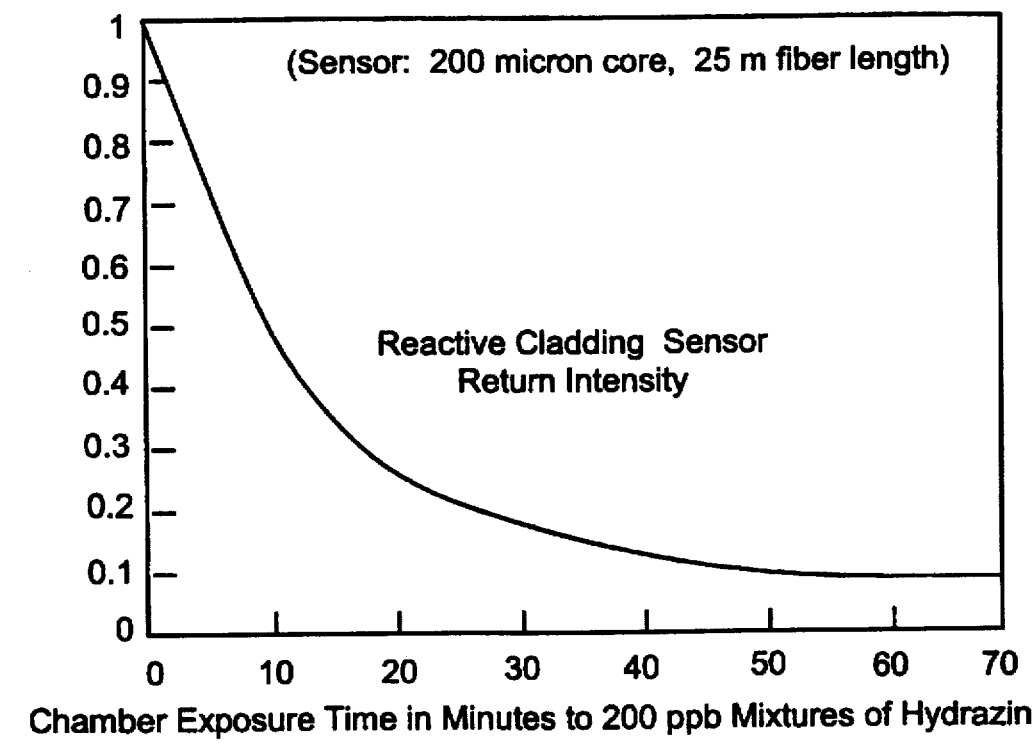
FIG. 7 is a graph of reactive cladding sensor return intensity.
Figure 8:
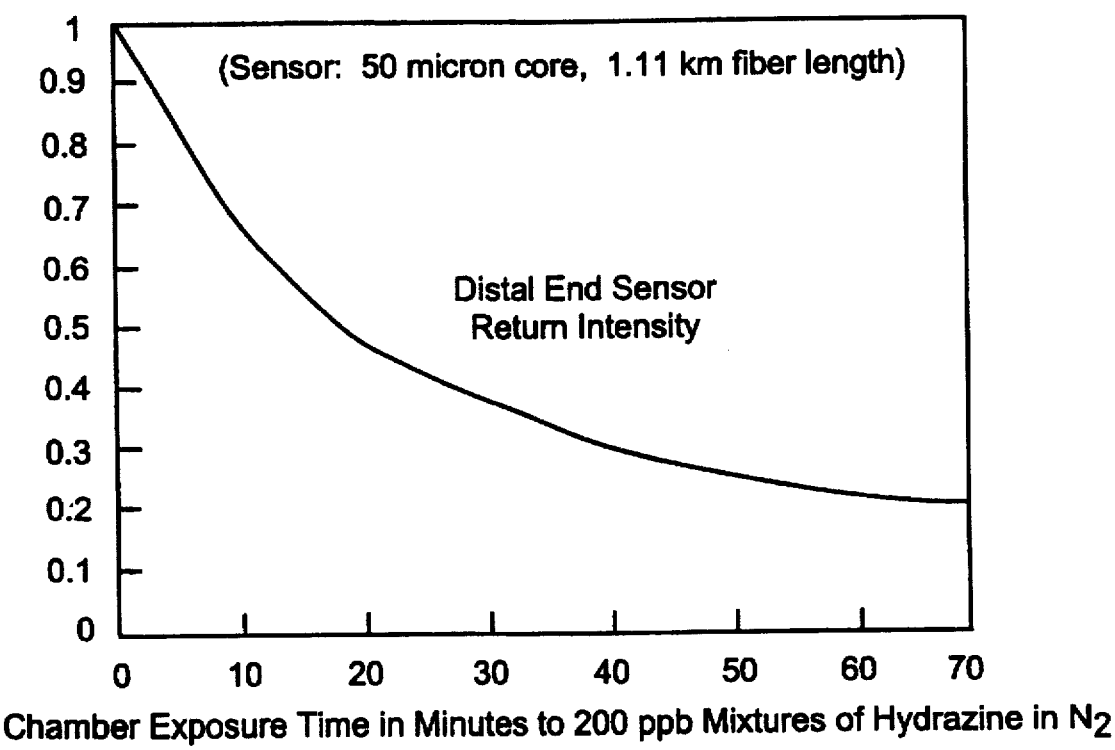
FIG. 8 is a graph of reactive distal end sensor return intensity.

Referring to FIGS. 3 through 8, the peak OTDR signal calibration returns 23 from the dosimeter sensor 16 normalized to the average peak power of the laser pulse 21 versus the exposure time of the sensor 16 in the hydrazine-fuel exposure chamber 49, is shown in FIGS. 6 through 8. Return results are measured by the reflectometer 51 for reactive cladding sensors 16 of FIG. 3 and distal end sensors of FIG. 4. These results are respectively shown in FIGS. 7 and 8.

Using PMA/Sol-Gel reactive cladding dosimeter sensors as shown in FIG. 3, the reflected return signal 23 has its highest level immediately after insertion into the chamber containing 200 ppb of hydrazine in $N_2$. After sealing the exposure chamber, the OTDR peak signal return 23 decays nearly completely over a period of about an hour, as shown in FIG. 7. The decay is due to the reaction of PMA with hydrazine to form the blue molybdenum oxide species that evanescently absorb the 680 nm laser light. A blank sol/gel-clad dosimeter that did not contain PMA may be used for verification to show the true extent of attenuation caused by the exposure of the PMA to the hydrazine. The PMA-clad dosimeter sensor demonstrated a significant decay in the intensity of the reflected return due to the occurrence of the colorimetric reaction. Inspection of the PMA-clad dosimeter after its removal from the chamber reveals a blue cladding. Analysis of the decay curve obtained with this PMA dosimeter sensor 16 yielded a detected dose at the five percent change level of two-hundred ppb-min. That is, a five percent change in the retro-reflected signal return 23 was observed when the dosimeter sensor was exposed to 200 ppb of hydrazine vapor for a one minute period. This detectivity is adequate for current sensing requirements but it might be considerably improved by increasing the concentration of PMA in the sol-gel, using longer reactive-clad regions, or by employing tapered or tightly coiled fiber dosimeter sensors that enhance evanescent wave coupling into the cladding.

Similar results were obtained using PMA/Sol-Gel distal end dosimeter sensors 16 of FIG. 4. For example, the calibration is performed with a fiber optic trunk line of 1.107 km in length that incorporated two PMA-coated dosimeters and a ten milliwatt, 780 nano-meter diode laser. The first dosimeter sensor 16 was exposed to laboratory air and was located at a distance of 1.1 km along the fiber optic trunk line. The second dosimeter sensor was located at a distance of 1.107 km and was placed inside the hydrazine exposure chamber. A plot of the normalized peak OTDR signal returns 23 from the second dosimeter versus its exposure time in the hydrazine chamber was also obtained by the reflectometer 51 as shown in FIG. 8. The signal returns 23 were observed to fall slightly immediately upon insertion and then to decline at approximately the same rate as the PMA-clad dosimeter sensor 16. No changes were observed during this exposure interval from the dosimeter that was exposed to laboratory air. The detectivity of the distal end dosimeter sensor 16 at the five percent change level was determined from the decay curve to be 400 ppb-min, a value that is comparable to the reactive clad dosimeter sensors 16. Repetition of calibration with a blank distal end coating yielded no observable changes in the reflected light signal returns 23 for verification of attenuation caused by the exposure to the hydrazine.

As may now be appreciated, the monitor 26 may be used to detect the time rate of change of the peak of the returns 23 to determine instantaneously the concentration of hydrazine fuels, whereas the peak value of the returns generally indicates the exposure dose amount. A fiber optic dosimeter system for detecting leaks of hydrazine-fuels vapors is capable of detecting a received hydrazine dose of 200 ppb-min in an evanescent operational mode and 400 ppb-min in a distal end mode. Similar detection sensitivities are possible for monomethylhydrazine and unsymmetrical dimethylhydrazine with this hydrazine-fuel fiber optic detection system. This performance already meets the Air Force's anticipated more stringent hydrazine-fuel dose detection requirements of 900 ppb-min. This system can be improved by optimizing dosimeter design. Remote detection at a distance of one kilometer is feasible. The performance of a multiplexed network containing hundreds of sensors can enhance field-scale fiber optic hydrazine detection systems.

The system is capable of determining dosimeter rejection against potential interferences such as $H_2O$, $NH_3$, organic solvents and other physical influences, for example, temperature, pressure, vibration and sensor aging. While the preferred sensor is a resettable PMA colorimeter sensor, various sensor structures, systems and method modifications and improvements may improve gas detection. Those improvements and modifications may nonetheless fall within the spirit and scope of the following claims.

We claim:

1. A system for detecting the presence of a gas over a predetermined area, said system comprising a diode laser means for generating a laser pulse, a fiber optic network connected to said diode laser means for communicating said laser pulse as an evanescent wave split and distributed within said predetermined area, a plurality of sensors means each having a reagent disposed therein distributed within said predetermined area for receiving said laser pulse and for absorbing and reflecting said laser pulse to provide a respective plurality of reflected returns amplitudinally changed by said plurality of sensors means when reacting to exposure of said gas through changes in optical absorption and reflection of said laser pulse by said reagent disposed in said plurality of sensors means, and a monitor means connected to said fiber optic network for receiving said plurality of reflected returns, and for correlating said plurality of reflected returns to said respective plurality of sensors means by time displacement and for determining by amplitudinal changes which ones of said plurality of sensors means have been exposed to said gas within said predetermined area.

2. The system of claim 1 wherein said laser pulse has a wavelength between 650 and 1000 nanometers.

3. The system of claim 1 wherein said gas is hydrazine and said reagent is phosphomolybdic acid (PMA).

4. The system of claim 1 wherein said laser pulse has a wavelength of 670 nanometers, said gas is a hydrazine fuel and said reagent is phosphomolybdic acid (PMA).

5. The system of claim 1 wherein said gas is nitrogen dioxide and said reagent is phosphomolybdic acid (PMA) saturated with a hydrazine fuel reducing agent.

6. The system of claim 1 wherein said gas is nitrogen tetroxide and said reagent is phosphomolybdic acid (PMA) saturated with a hydrazine fuel reducing agent.

7. The system of claim 1 further comprising fiber optic trunk means connected to said diode laser means for communicating said laser pulse to said fiber optic network, a pulser means for providing a reference pulse communicated to said diode laser means for activating said diode laser means to generate said laser pulse, said reference pulse further communicated to said monitor means for providing a time reference of said laser pulse, and a fiber optic coupler means connected between said fiber optic network and said fiber optic trunk means for communicating said laser pulse from said fiber optic trunk means to said fiber optic network and for communicating said plurality of reflected returns to said monitor means.

8. The system of claim 1 wherein said fiber optic network comprises an optical fiber having a plurality of fiber optical branches extending from said optical fiber at a plurality of points along said optical fiber, said plurality of optical fiber branches have said respective plurality of sensor means located at respective distal ends of said optical fiber branches.

9. A method for detecting the presence of a gas over a predetermined area, said method comprising steps of generating a laser pulse, distributing a laser pulse through a distributive fiber optic network to a plurality of sensors each having a reagent that reacts with said gas to change said reagent to a state which optically absorbs said laser pulse, reflecting returns dependent upon exposure to said gas to said plurality of sensors, receiving said returns, determining respective time displacements from said generation step until said receiving step for said returns, correlating said returns to respective ones of said sensors by time displacement from said generating step to said receiving step, measuring amplitudinal changes of said returns caused by said exposure to said gas, and determining which ones of said sensors disposed at respective points within said wide area have been exposed to said gas.

10. The method of claim 9 wherein said laser pulse has a wavelength of 670 nanometers, said gas is a hydrazine fuel, and said reagent is phosphomolybdic acid (PMA).

11. The method of claim 9 wherein said gas is nitrogen dioxide, said reagent is phosphomolybdic acid (PMA) saturated with a hydrazine fuel reducing agent.

12. The method of claim 9 wherein said gas is nitrogen tetroxide, and said reagent is phosphomolybdic acid (PMA) saturated with a hydrazine fuel reducing agent.

13. The method of claim 9 further comprising steps of, measuring amplitudes of said returns for said sensors absent exposure to said gas, and exposing said sensors to said gas, measuring amounts of exposure of said sensors to said gas, measuring amplitudinal changes of said returns correlated to said amounts of exposure, and calibrating said sensors to said amounts of exposure correlated to said amplitudinal changes.

14. The method of claim 9 further comprising the steps of repeating said generating, distributing, receiving, determining and measuring steps a plurality of times, and said determining step determines time rate of changes of said returns to indicate gas concentrations respectively at said sensors.

* * * * *